(12) United States Patent
Genovese et al.

(10) Patent No.: US 12,262,927 B2
(45) Date of Patent: Apr. 1, 2025

(54) SCREW INSERTION INSTRUMENT AND METHODS OF USE

(71) Applicant: K2M, Inc., Leesburg, VA (US)

(72) Inventors: Daniel Genovese, Great Falls, VA (US); Erica Lynn Marron, Leesburg, VA (US); Joshua David Rubin, Reston, VA (US); Andrew Kam, Westmead (AU)

(73) Assignee: K2M, Inc., Leesburg, VA (US)

( * ) Notice: Subject to any disclaimer, the term of this patent is extended or adjusted under 35 U.S.C. 154(b) by 364 days.

(21) Appl. No.: 17/544,363

(22) Filed: Dec. 7, 2021

(65) Prior Publication Data

US 2022/0183726 A1 Jun. 16, 2022

Related U.S. Application Data

(60) Provisional application No. 63/123,772, filed on Dec. 10, 2020.

(51) Int. Cl.
*A61B 17/70* (2006.01)
*A61B 17/86* (2006.01)

(52) U.S. Cl.
CPC ...... *A61B 17/7082* (2013.01); *A61B 17/7091* (2013.01); *A61B 17/86* (2013.01)

(58) Field of Classification Search
CPC ............ A61B 17/8891; A61B 17/8886; A61B 17/888; A61B 17/8875; A61B 17/8872; A61B 17/8841; A61B 17/8819; A61B 17/7076; A61B 17/7074
See application file for complete search history.

(56) References Cited

U.S. PATENT DOCUMENTS

| | | | |
|---|---|---|---|
| 4,838,282 A | 6/1989 | Strasser et al. | |
| 5,189,422 A | 2/1993 | van de Plassche et al. | |
| 5,423,819 A | 6/1995 | Small et al. | |
| 5,484,440 A | 1/1996 | Allard | |
| 5,549,931 A | 8/1996 | Dattatraya et al. | |
| 5,946,988 A | 9/1999 | Metz-Stavenhagen | |
| 6,312,394 B1 | 11/2001 | Fleming, III | |

(Continued)

FOREIGN PATENT DOCUMENTS

| | | |
|---|---|---|
| EP | 2939621 A1 | 11/2015 |
| EP | 3501438 A1 | 6/2019 |

(Continued)

OTHER PUBLICATIONS

Extended European Search Report issued in EP Appln. No. 21213255.9 mailed May 16, 2022 (2 pages).

*Primary Examiner* — Eduardo C Robert
*Assistant Examiner* — Michelle C Green
(74) *Attorney, Agent, or Firm* — Lerner David LLP

(57) ABSTRACT

A screw driving instrument is provided with a stylet holder able to retain a head of a stylet at one of multiple discrete locations. A user may vary a distance that a point of the stylet extends from a distal end of the instrument by choosing which of the discrete locations to insert the stylet head into before coupling the stylet holder to the instrument. The instrument may include a ratcheting handle capable of rotation in one direction about a central axis of the instrument relative to other components of the instrument. The stylet holder may be engageable with the handle.

19 Claims, 13 Drawing Sheets

(56) References Cited

U.S. PATENT DOCUMENTS

| | | |
|---|---|---|
| 6,436,100 B1 | 8/2002 | Berger |
| 6,827,722 B1 | 12/2004 | Schoenefeld |
| 7,296,500 B1 | 11/2007 | Martinelli |
| 7,572,264 B2 | 8/2009 | Null et al. |
| 7,758,584 B2 | 7/2010 | Bankoski et al. |
| 7,846,093 B2 | 12/2010 | Gorek et al. |
| 7,947,048 B2 | 5/2011 | Doll et al. |
| 8,002,798 B2 | 8/2011 | Chin et al. |
| 8,062,340 B2 | 11/2011 | Berrevoets et al. |
| 8,075,579 B2 | 12/2011 | Hamada |
| 8,100,916 B2 | 1/2012 | Kumar et al. |
| 8,221,431 B2 | 7/2012 | Chenaux |
| 8,231,635 B2 | 7/2012 | Sharifi-Mehr et al. |
| 8,262,662 B2 | 9/2012 | Beardsley et al. |
| 8,273,089 B2 | 9/2012 | Jackson |
| 8,308,729 B2 | 11/2012 | Nunley et al. |
| 8,343,165 B2 | 1/2013 | Berrevoets |
| 8,377,065 B2 | 2/2013 | Kuntz et al. |
| 8,394,108 B2 | 3/2013 | McLean et al. |
| 8,460,307 B2 | 6/2013 | Saidha et al. |
| 8,485,075 B1 | 7/2013 | Gauthier et al. |
| 8,512,344 B2 | 8/2013 | Hoffman et al. |
| 8,663,292 B2 | 3/2014 | Dec et al. |
| 8,714,056 B2 | 5/2014 | Landowski |
| 8,715,293 B2 | 5/2014 | Vandewalle |
| 8,747,411 B2 | 6/2014 | Mitchell |
| 8,814,914 B2 | 8/2014 | Miller et al. |
| 8,852,239 B2 | 10/2014 | Jackson et al. |
| 8,858,605 B1 | 10/2014 | Glatzer et al. |
| 8,894,655 B2 | 11/2014 | Fallin et al. |
| 9,131,946 B2 | 9/2015 | Larche et al. |
| 9,242,357 B2 | 1/2016 | Nino et al. |
| 9,254,160 B2 | 2/2016 | Pakzaban et al. |
| 9,409,285 B2 | 8/2016 | Vinson et al. |
| 9,433,445 B2 | 9/2016 | Ramsay et al. |
| 9,451,954 B2 | 9/2016 | Moore et al. |
| 9,526,553 B2 | 12/2016 | Bess et al. |
| 9,750,508 B1 | 9/2017 | Barnes et al. |
| 9,855,087 B2 | 1/2018 | Divincenzo et al. |
| 9,877,764 B2 | 1/2018 | Nino et al. |
| 10,194,967 B2 | 2/2019 | Baynham |
| 10,219,845 B2 | 3/2019 | Petit |
| RE47,348 E | 4/2019 | Chin et al. |
| 10,413,339 B2 | 9/2019 | Ramsay et al. |
| 10,433,883 B2 | 10/2019 | DiVincenzo et al. |
| 10,575,888 B2 | 3/2020 | Coillard-Lavirotte et al. |
| 10,667,849 B2 | 6/2020 | Koenig et al. |
| 10,687,881 B2 | 6/2020 | Paroth et al. |
| 11,045,232 B2 * | 6/2021 | Fischer .............. A61B 17/7088 |
| 2002/0091386 A1 | 7/2002 | Martin et al. |
| 2004/0138662 A1 | 7/2004 | Andry et al. |
| 2005/0137601 A1 | 6/2005 | Assell et al. |
| 2006/0122597 A1 | 6/2006 | Jones et al. |
| 2007/0239159 A1 | 10/2007 | Altarac et al. |
| 2008/0045970 A1 | 2/2008 | Saidha et al. |
| 2008/0243133 A1 | 10/2008 | Heinz |
| 2009/0187194 A1 | 7/2009 | Hamada |
| 2009/0187220 A1 | 7/2009 | Hamada |
| 2009/0264895 A1 | 10/2009 | Gasperut et al. |
| 2009/0275954 A1 | 11/2009 | Phan et al. |
| 2010/0036381 A1 | 2/2010 | Vanleeuwen et al. |
| 2010/0204703 A1 | 8/2010 | Gao |
| 2010/0298838 A1 | 11/2010 | Walters |
| 2011/0054537 A1 | 3/2011 | Miller et al. |
| 2011/0257690 A1 | 10/2011 | Rezach |
| 2012/0055296 A1 | 3/2012 | Landowski |
| 2012/0198972 A1 | 8/2012 | Nino et al. |
| 2012/0203287 A1 | 8/2012 | Arambula et al. |
| 2012/0203288 A1 | 8/2012 | Lange et al. |
| 2012/0239052 A1 | 9/2012 | Beger et al. |
| 2013/0013003 A1 | 1/2013 | Carbone et al. |
| 2013/0276597 A1 | 10/2013 | Ivinson et al. |
| 2013/0276598 A1 | 10/2013 | Ivinson et al. |
| 2013/0310842 A1 | 11/2013 | Winkler et al. |
| 2013/0327190 A1 | 12/2013 | Laurenti et al. |
| 2014/0194886 A1 | 7/2014 | Poulos |
| 2014/0276891 A1 | 9/2014 | Defalco et al. |
| 2014/0276893 A1 | 9/2014 | Schaller et al. |
| 2014/0277164 A1 * | 9/2014 | Ramsay ............. A61B 17/7076 606/279 |
| 2014/0277188 A1 | 9/2014 | Poulos |
| 2014/0277206 A1 | 9/2014 | Reitblat et al. |
| 2014/0277212 A1 | 9/2014 | Dauster |
| 2014/0324062 A1 | 10/2014 | Heuer et al. |
| 2014/0330315 A1 | 11/2014 | Butler et al. |
| 2015/0066084 A1 | 3/2015 | Petit |
| 2015/0094781 A1 | 4/2015 | Paroth et al. |
| 2015/0164540 A1 | 6/2015 | Higgins et al. |
| 2015/0164569 A1 | 6/2015 | Reitblat et al. |
| 2015/0250521 A1 | 9/2015 | Poker et al. |
| 2015/0282855 A1 | 10/2015 | Bess et al. |
| 2015/0367487 A1 | 12/2015 | Nino et al. |
| 2016/0030100 A1 * | 2/2016 | Divincenzo ........ A61B 17/7082 606/104 |
| 2016/0101508 A1 | 4/2016 | Cutler |
| 2016/0296266 A1 | 10/2016 | Chandanson et al. |
| 2016/0354906 A1 | 12/2016 | Nino et al. |
| 2017/0105813 A1 | 4/2017 | Rash et al. |
| 2017/0128116 A1 | 5/2017 | Hansell et al. |
| 2017/0217000 A1 | 8/2017 | Dierickx et al. |
| 2017/0333093 A1 | 11/2017 | Krier et al. |
| 2018/0092671 A1 | 4/2018 | Krause et al. |
| 2018/0133871 A1 | 5/2018 | Farmer |
| 2018/0146982 A1 | 5/2018 | Brockman et al. |
| 2018/0146990 A1 | 5/2018 | Manzanares et al. |
| 2018/0177536 A1 | 6/2018 | Divincenzo et al. |
| 2018/0235677 A1 | 8/2018 | Kam et al. |
| 2018/0368892 A1 | 12/2018 | Marnay |
| 2018/0368893 A1 * | 12/2018 | DiVincenzo ........ A61B 17/7082 |
| 2019/0022833 A1 | 1/2019 | Macke et al. |
| 2019/0083147 A1 | 3/2019 | Hackathorn, II |
| 2019/0125421 A1 * | 5/2019 | Smith ................ A61B 17/8875 |
| 2019/0247102 A1 | 8/2019 | Biedermann |
| 2019/0298416 A1 | 10/2019 | Rezach |
| 2019/0336180 A1 | 11/2019 | Cahill |
| 2020/0093530 A1 * | 3/2020 | Klausman .......... A61B 17/8875 |
| 2020/0268427 A1 | 8/2020 | Muser et al. |
| 2020/0281608 A1 * | 9/2020 | Sharifi-Mehr ....... A61B 17/848 |
| 2021/0228245 A1 * | 7/2021 | Geist .................. A61B 17/8872 |
| 2021/0244424 A1 * | 8/2021 | Suchomel ............. A61B 90/03 |
| 2022/0061895 A1 * | 3/2022 | Kibrya .............. A61B 17/7082 |

FOREIGN PATENT DOCUMENTS

| | | |
|---|---|---|
| WO | 2015186080 A2 | 12/2015 |
| WO | 2017127502 A1 | 7/2017 |
| WO | 2019/002992 A1 | 1/2019 |

* cited by examiner

SCREW INSERTION INSTRUMENT AND METHODS OF USE

CROSS-REFERENCE TO RELATED APPLICATION

This application claims the benefit of the filing date of U.S. Provisional Patent Application No. 63/123,772 filed Dec. 10, 2020, the disclosure of which is hereby incorporated herein by reference.

BACKGROUND

Spinal fixation apparatus are widely employed in surgical processes for correcting spinal injuries and diseases. For instance, in order to facilitate stabilizing the spine and maintaining vertebral bodies in a desired alignment, implants, such as longitudinally linked rods, are secured to coupling elements which, in turn, are secured to vertebral bodies by fasteners, such as pedicle screws.

Many pedicle screws utilize a coupling element or tulip, which engages the pedicle screw head and is pivotable and/or rotatable in relation to the axis of the screw shank (e.g., polyaxial to the shank axis). While this ability more easily facilitates alignment of the tulip with the longitudinally linked rods, it may cause the pedicle screw to be difficult to handle. The use of an insertion instrument typically provides more positive control over the placement of the pedicle screw.

Prior to the placement of the pedicle screw into the vertebral body, many insertion instruments utilize devices, such as, for example, a guidewire or K-wire to aid in the introduction of the pedicle screw into the vertebral body and to control its trajectory so that it may be more accurately secured to the vertebral body.

Screw insertion instruments exist that use a stylet in place of a guidewire for introducing the pedicle screw into the vertebral body. Such instruments hold the stylet and screw at fixed positions such that the stylet extends distally from the tip of the screw by a small distance. Because pedicle screws are available in various lengths, a screw insertion instrument capable of holding the stylet at a variable location may be advantageous in certain situations.

BRIEF SUMMARY

In an aspect of the disclosure, a stylet holder may be releasably couplable with a cannulated screw driving instrument. The stylet holder may be able to retain a stylet head at one of multiple discrete locations, such that a user may vary a distance that a point of the stylet extends from a distal end of the instrument by choosing which of the discrete locations to insert the stylet head into before coupling the stylet holder to the instrument. The stylet holder may include a channel extending along an axis, and the multiple discrete locations may be defined by ribs opposed sides of the channel. The stylet holder may further include a series of apertures, each aperture opening into the channel at one of the multiple discrete locations. The stylet holder may be couplable to the instrument by inserting the stylet, followed by the stylet holder, into a cannulation of the instrument while the stylet head is retained within one of the multiple discrete locations within the stylet holder.

The instrument may include a ratcheting handle capable of rotation in one direction about a central axis of the instrument relative to other components of the instrument. A ratcheting function of the handle may be provided by a gear disposed within the handle, and a pawl fixed to the handle shaped to allow the gear to rotate relative to the handle in only one direction about the central axis. The handle may be lockable to reversibly disable the ratcheting function. The ratcheting function may be reversibly disabled by actuation of a post moveable radially relative to the central axis. The post may include post on a radially inner end, and the post teeth may engage the gear when the post is in a radially inner position. The handle may include a retainer biased to engage the post when the post is in the radially inner position to prevent the post from travelling out of the radially inner position. The retainer may be manipulable to release the post from the radially inner position, and the post may be biased to move to a radially outer position when released by the retainer. The gear may be engageable by a clip of the stylet holder to facilitate the releasable coupling between the stylet holder and the instrument. The gear may include an annular groove, and the clip may be moveable between a position wherein it may engage the annular groove and a position wherein it may not engage the annular groove.

In another aspect, screw driving instrument may include a handle, a passage extending through the handle and along a central axis of the instrument, and an insert receivable in a portion of the passage extending through the handle. The insert may include a clip engageable to the handle, a pillar including a channel extending axially to define an elongate slot on one side of the pillar, and axial column of recesses on at least one side of the channel.

In some arrangements, the recesses may be defined by a column of radially extending ribs on the at one side of the channel.

In some arrangements, the instrument may include a column of apertures opening into the channel and extending along an opposite side of the pillar from the elongate slot, each aperture being axially aligned with one of the recesses.

In some arrangements, the instrument may include opposed pairs of recesses defined on two sides of the channel.

In some arrangements, the instrument may include a column of apertures opening into the channel and extending along an opposite side of the pillar from the elongate slot, each aperture being axially aligned with one of the opposed pairs of recesses on the sides of the channel.

In some arrangements, the handle may include a ratchet mechanism. The ratchet mechanism may include a gear disposed within a body of the handle and including an axial bore through which the insert is insertable. The ratchet mechanism may further include a pawl fixed to the handle allowing rotation of the body of the handle relative to the gear in only one direction about the central axis of the instrument.

In some arrangements, the ratchet mechanism may comprise a post disposed within the body of the handle and having a radially inner end with post teeth. The post may be actuatable between a radially inner position wherein the post teeth engage the gear and prevent rotation of the body of the handle relative to the gear about the central axis of the instrument and a radially outer position wherein the post teeth do not engage the gear.

In another aspect, a screw driving instrument may include a cannulated drive shaft including a distal end defining a drive head and extending along a central axis of the instrument. The instrument may further include a stylet including a proximal end defining a stylet head. The instrument may further include a stylet holder engageable to the instrument and including a pillar configured to retain the stylet head at one of a variety of discrete positions relative to the instrument while the stylet holder is coupled to the instrument.

In some arrangements, the stylet holder may be couplable to the instrument such that the stylet head may not be removable from the pillar while the stylet holder is coupled to the instrument.

In some arrangements, the instrument may include a ratcheting handle.

In some arrangements, the ratcheting handle may be releasably engageable with the drive shaft.

In some arrangements, the handle may include a gear and pawl assembly providing ratcheting function to the handle, the gear including a bore through which the pillar is received while the stylet holder is coupled to the instrument.

In some arrangements, reversible coupling between the stylet holder and the instrument may be facilitated by a clip of the stylet holder being engageable with the gear.

In some arrangements, the handle may be reversibly lockable such that ratcheting is prevented while the handle is locked.

In another aspect, a method of use of a screw driving instrument may include disposing a portion of a stylet within a stylet holder capable of retaining the portion of the stylet at multiple locations along an axis such that the portion of the stylet is retained at one of the multiple locations along the axis. The method may further include inserting the stylet and stylet holder into the instrument such that a distal end of the stylet extends out of a distal end of the instrument while the portion of the stylet is retained at the one of the multiple locations along the axis.

In some arrangements, the method may include creating a pilot hole in a solid object with the stylet, and introducing a screw into the pilot hole with the instrument. The method may further include removing the stylet holder and stylet from the instrument after introducing the screw into the pilot hole.

In some arrangements, the stylet holder may be removed from the instrument by use of opposed ends of a removal tool to simultaneously depress a button to decouple the stylet holder from the instrument with one of the opposed ends and wedge between the instrument and stylet holder with another of the opposed ends.

In some arrangements, the multiple locations may be discrete and predefined.

In some arrangements, the multiple locations along the axis may be predefined by recesses extending axially along at least one side of a channel extending along a portion of the stylet holder.

In some arrangements, the instrument may include a ratcheting handle capable of being locked to reversibly disable ratcheting.

DETAILED DESCRIPTION

When referring to specific directions and planes in the following disclosure, it should be understood that, as used herein, the term "proximal" means closer to the operator/surgeon, and the term "distal" means further away from the operator/surgeon.

Figure 1A:
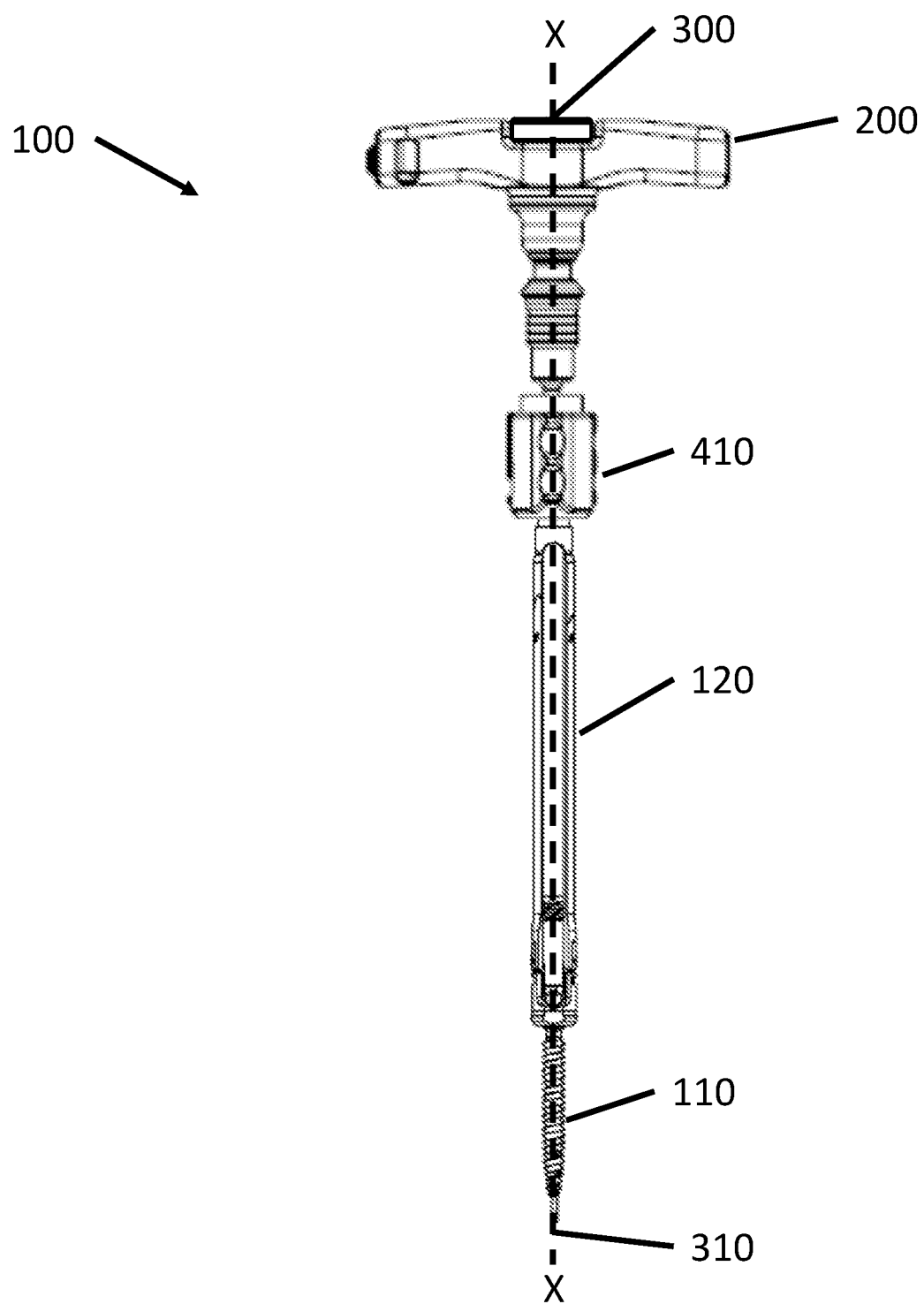
FIG. 1A is a side elevation view of a screw driving instrument according to an aspect of the disclosure in a fully assembled state.
Figure 1B:
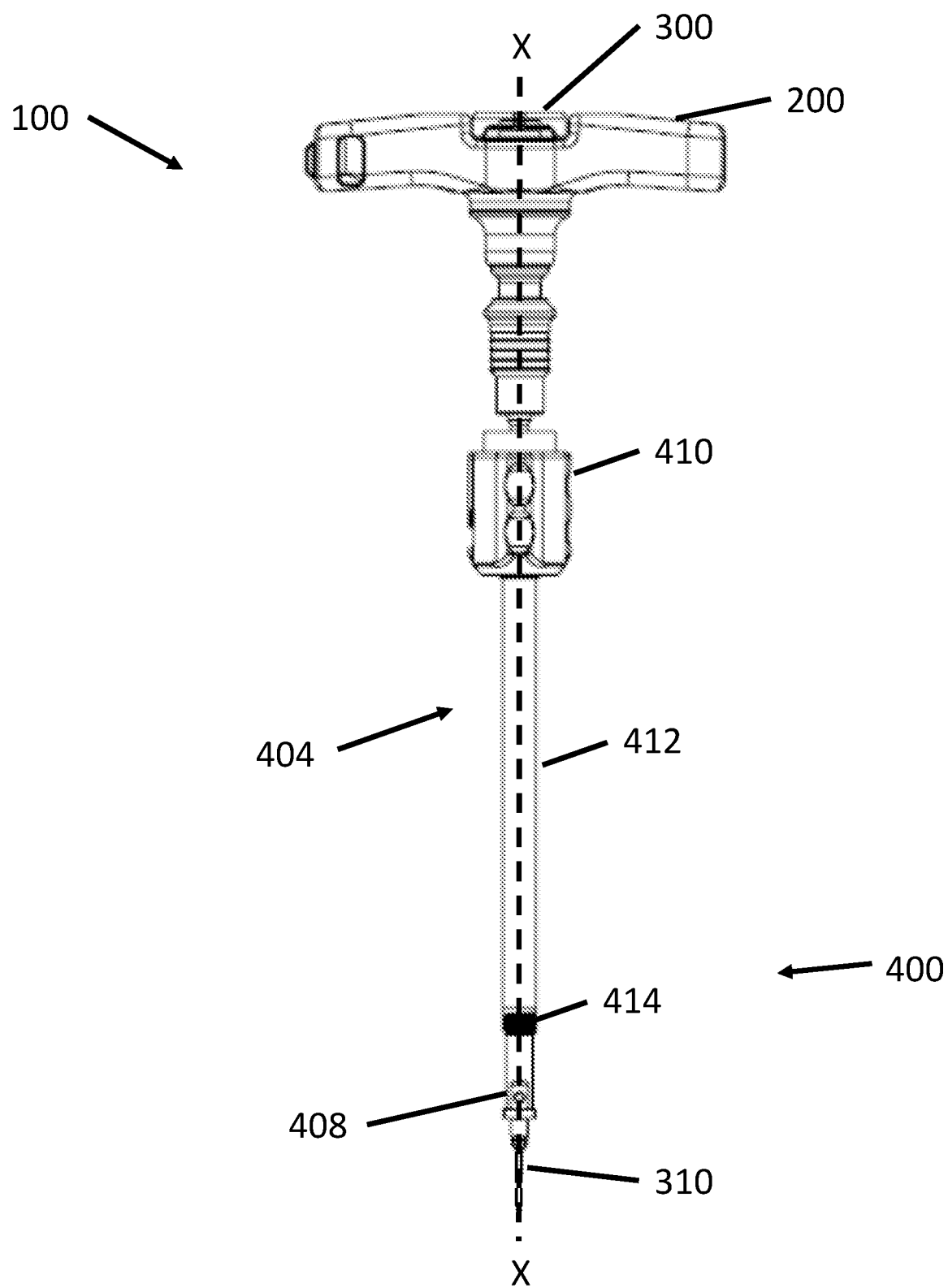
FIG. 1B is the side elevation view of the instrument of FIG. 1A in a partially disassembled state.

A screw driving instrument 100 for inserting a screw, such as a cannulated pedicle screw 110, into an object, such as a vertebral pedicle, is illustrated in a fully assembled state in FIG. 1A, and in a state that is fully assembled except for the pedicle screw 110 and an extension assembly 120 in FIG. 1B. The instrument 100 and its components extend generally along a central axis X. As used herein, the terms "axial," "radial," and "tangential" refer to directions relative to the central axis X, except where specified otherwise. Further, where the central axis X is illustrated with regard to any component of the instrument 100 in FIGS. 2A-6, it indicates that component's orientation relative to the central axis X in the fully assembled state of the instrument 100 as shown in FIG. 1A.

The instrument 100 includes a ratcheting handle 200 at its proximal end, with a stylet holder 300 disposed through the handle 200. A stylet 310 extends along the central axis X from a proximal end of the stylet holder 300 to a distal tip of the stylet 310 that extends distally beyond a distal tip of the attached pedicle screw 110. A drive assembly 400 is connected at a distal end of the handle 200. As shown in FIG. 1B, the drive assembly 400 includes a sheath assembly 404 and a cannulated driver 408 that extends proximally from the sheath assembly 404 into the handle 200 and distally from the sheath assembly 404 to drive the pedicle screw 110. The sheath assembly 408 further includes a knob 410 near its proximal end and a tube 412 extending through and distally beyond the knob 410. The tube 412 as shown in FIG. 1B includes a threaded section 414 at its distal end, but in alternative arrangements the tube 412 may include other coupling features, and in further arrangements the threaded section 414 or other coupling features may be located away from the distal end of the tube 412.

Returning to FIG. 1A, an extension assembly 120 may be coupled to the drive assembly 400, such as by internal threading engaged with the threaded section 414 of tube 412, or by other coupling features the extension assembly 120 and tube 412 may have. The extension assembly 120 holds a head or tulip feature of the pedicle screw 110 at a distal position relative to the drive assembly 400 such that the driver 408 may drivingly engage the pedicle screw 110.

For a more detailed description of a similar drive assembly, extension assembly, and pedicle screw, and of the interaction of those components, reference can be made to U.S. Pat. Pub No. 2018/0353224 (hereinafter the '224 publication), filed Jun. 12, 2018, the entirety of which is incorporated by reference herein. For a more detailed description of the interaction between drive and extension assemblies specifically, reference can be made to U.S. Pat. No. 8,308,729 (hereinafter the '729 patent), filed Jun. 11, 2009, and for a more detailed description of a similar drive assembly alone, reference can be made to U.S. Pat. No. 9,526,553 (hereinafter the '553 patent), filed Apr. 4, 2014. For a more detailed description of an exemplary bone screw that may be compatible with the instrument 100 of the present disclosure if modified at least with cannulation, reference can be made to U.S. Pat. Pub. No. 2013/0013003 (hereinafter the '003 publication), filed on Sep. 26, 2012, though it should be understood that the instrument 100 is compatible with a broad variety of cannulated screws known and unknown in the art. The entirety of the '729 and '553 patents and the '224 and '003 publications are also incorporated by reference herein.

Figure 2A:
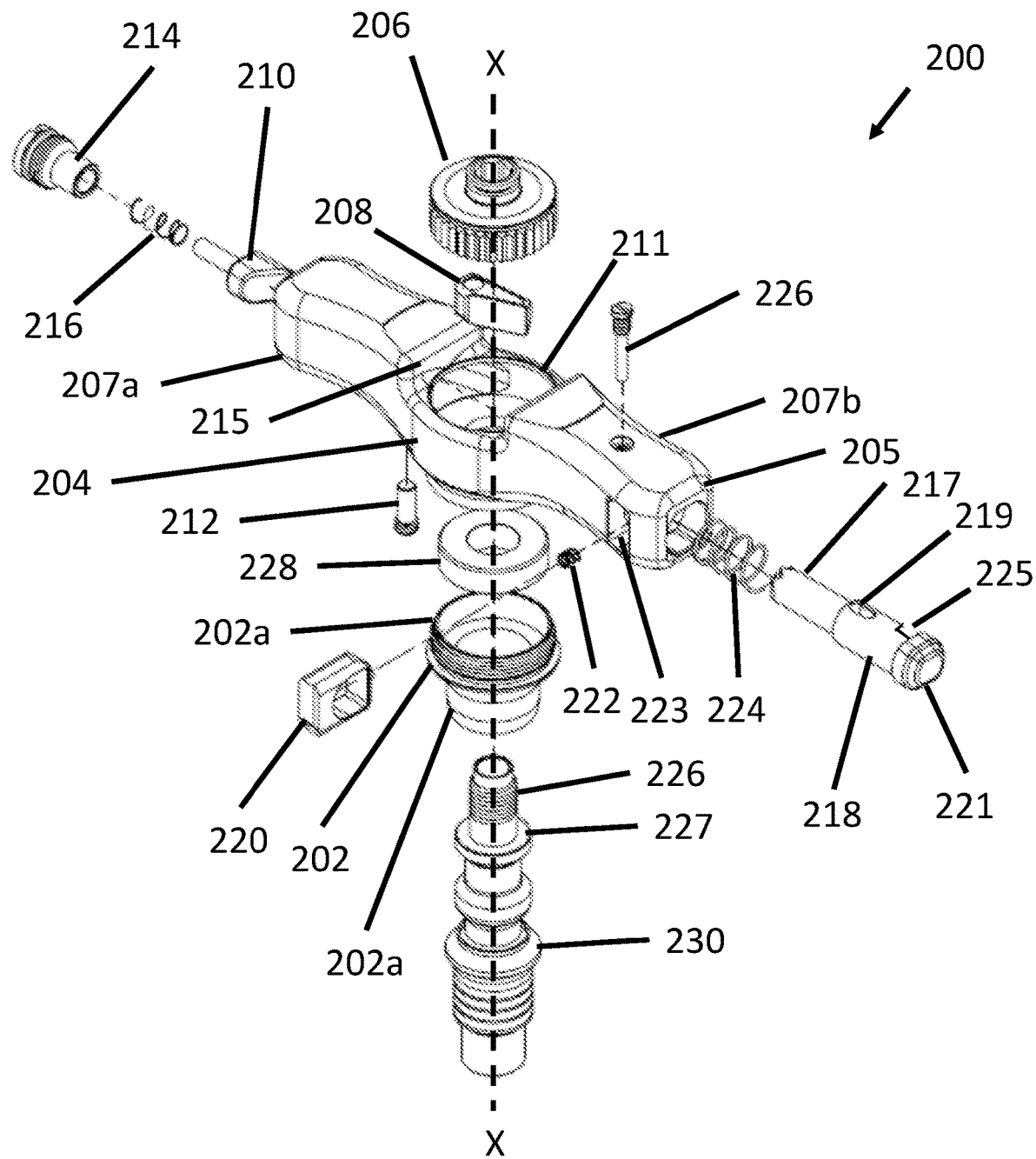
FIG. 2A is an exploded perspective view of a handle of the instrument of FIGS. 1A and 1B.
Figure 2B:
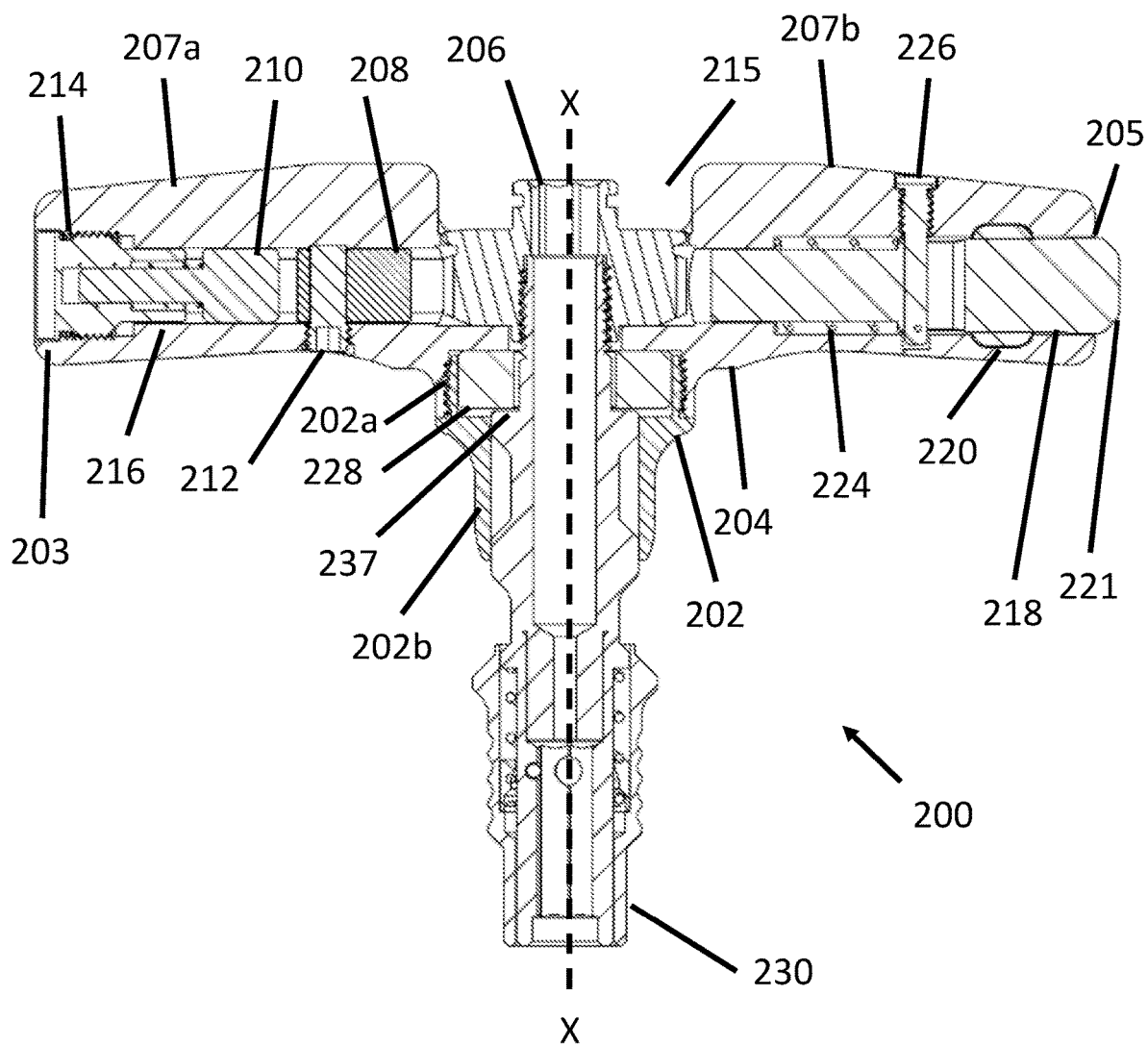
FIG. 2B is a cross-sectional elevation view of the handle of FIG. 2A in a fully assembled state.

An exemplary arrangement of parts for the ratcheting handle 200 is illustrated in FIG. 2A, with a cross-section of the fully assembled handle 200 shown in FIG. 2B. In an exemplary method of assembling the handle 200, a pawl 208 is inserted into a cavity 211 in a body 204 of the handle 200. The body 204 includes a first arm 207a and a second arm 207b extending in mutually opposite radial directions. The cavity 211 extends from a first opening 203 shown FIG. 2B at a radial extremity of the first arm 207a to a second opening 205 at a radial extremity of the second arm 207b. A handle recess 215 at a proximal side of the body 204 opens distally into the cavity 211.

The pawl 208 is positioned within the first arm 207a such that the pawl tapers to be narrower with increasing proximity to the central axis X. The pawl 208, once positioned, is secured with a pawl pin 212 that may be inserted through a corresponding hole in the first arm 207a of the body 204. The pawl pin 212 of the illustrated arrangement includes threading for engaging threads in the corresponding hole in the first arm 207a. The pawl pin 212 fixes the pawl 208 in place within the first arm 207a, but the pawl 208 is able to pivot about the pawl pin 212.

A washer 228 is inserted into a disc shaped space within an externally threaded proximal annulus 202a of a proximal adapter 202. The proximal annulus 202a is then threaded into a threaded distal opening of the body 204. A gear 206 is inserted into the cavity 211 through the handle recess 215. An externally threaded neck 236 of a distal adapter 230 is inserted through the proximal adapter 202 and washer 228 into the cavity 211 and threaded into an internal bore of the gear 206. A flat radial shoulder 227 of the distal adapter 230 seats against the washer 228 to prevent the gear 206 from moving axially after the neck 226 is threaded into the washer 228 while allowing the gear 206 and distal adapter 230 to rotate smoothly about the central axis X.

Figure 2C:
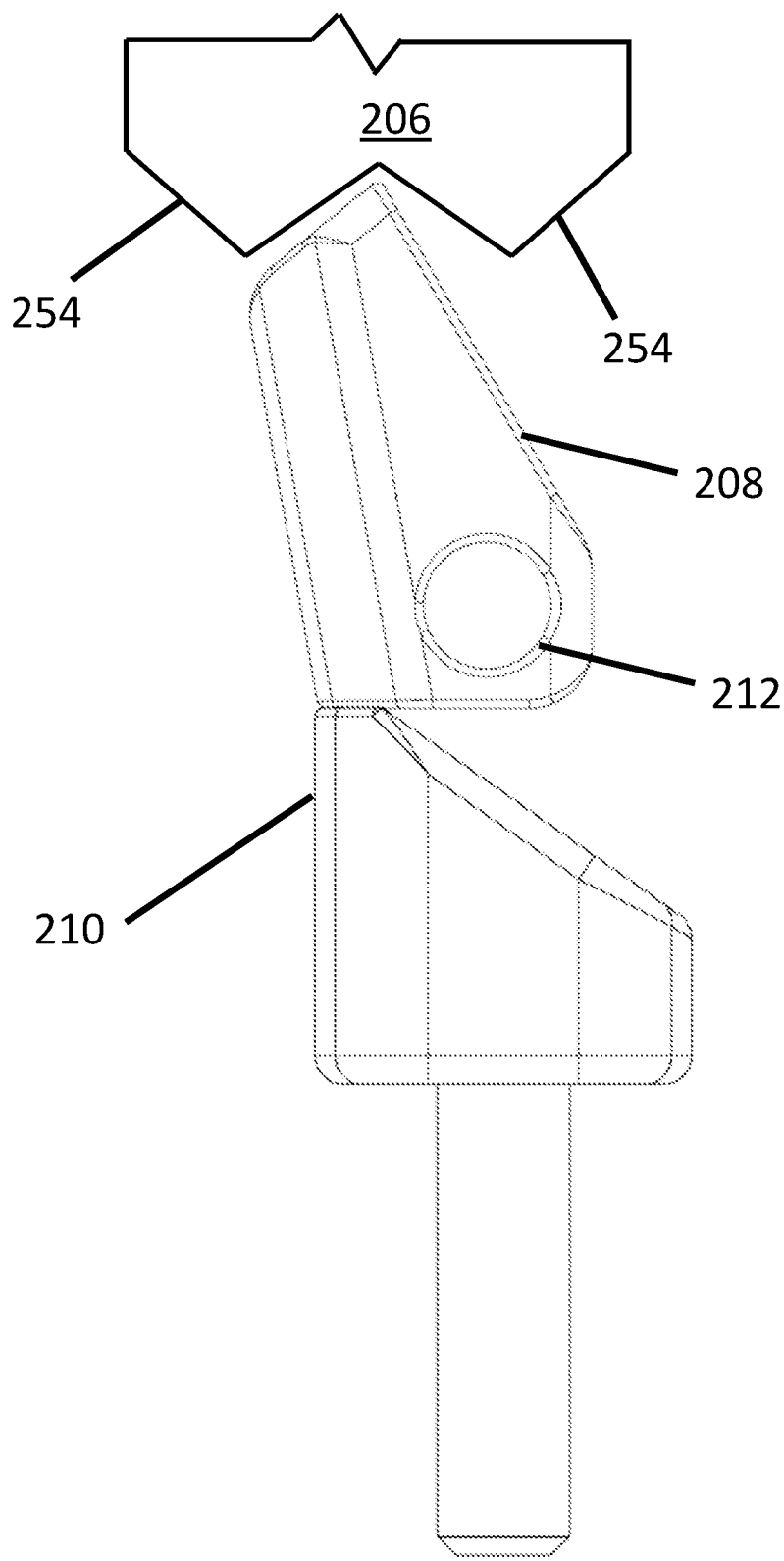
FIG. 2C is a top view of a portion of a pawl and gear assembly located within the handle of FIGS. 2A and 2B.

A block 210 is inserted into the first opening 203, followed by a block spring 216 and a lock screw 214. The lock screw 214 is threaded into the first opening 203 to close the first opening 203 and hold the block spring 216 against the block 210. The pawl 208, block 210, and gear 206 are thus positioned with respect to one another within the cavity 211 approximately as shown in FIG. 2C. The pawl 208 is asymmetrical to permit the gear 206 to rotate in only one direction about the central axis X. More specifically, the pawl 208 is shaped and located such that, if the gear 206 rotates in a counter-clockwise direction from the perspective of FIG. 2C, a gear tooth 254 will act to compress the pawl 208 against the pawl pin 212, causing the gear 206 against the pawl 208. However, if the gear 206 rotates in a clockwise direction from the perspective of FIG. 2C, the pawl 208 will pivot about the pawl pin 212 and permit the gear teeth 206 to pass by. When rotation of the gear 206 causes the pawl 208 to pivot, the pawl 208 pushes the block 210 back toward the lock screw 214. The block spring 216 pushes back on the block 210 to cause the block 210 to push, in turn, on the pawl 208, thereby causing the pawl 208 to return to position between each gear tooth 254 when the gear 206 rotates. The block 210 and block spring 212 thereby prevent the pawl 208 from skipping over gear teeth 254 and ensures rotation of the gear 206 in the binding direction will consistently be prohibited.

Because the pawl pin 208 is fixed within the first arm 207a of the body 204, but the gear 206 is free to rotate relative to the body 204, the foregoing description of FIG. 2C similarly to movement of the body 204 relative to the gear 206. In other words, the pawl 208 permits the body 204 to be rotated relative to the gear 206 in a counter-clockwise direction from the perspective of FIG. 2C, but not in a clockwise direction. As such, if there is resistance on the gear 206 through the adapters 202, 230, torque applied to the body 204 in the counter-clockwise direction is not transferred to the adapters 202, 230, but torque applied to the body 204 in the clockwise direction is applied to the adapters 202, 230 by action of the pawl 212 against the gear 206.

In continued reference to FIGS. 2A and 2B, a retainer spring 222 is inserted into the cavity 211 through a second arm aperture 223 on a surface of the second arm 207b, followed by a retainer 220. Next, a lock post spring 224 is inserted into the cavity 211 through the second opening 205 and retainer 220, and a lock post 218 is inserted through the second opening 205, lock post spring 224, and retainer 220. The lock post 218 is secured within the cavity by inserting a lock post pin 226 through a corresponding hole in the second arm 207b of the body 204 and through a post track 219 defined through the lock post 218. In the illustrated arrangement, the lock post pin 226 includes threads for engaging threads of the corresponding hole in the second arm 207b. Securing the lock post 218 within the cavity 211 also prevents the retainer 220 from being removed through the second arm aperture 223.

The lock post 218 and retainer 220 cooperate to selectively lock and release the body 204 relative to the gear 206. A radially inner end of the lock post 218 includes post teeth 217 for engaging the gear 206. The post track 219 permits some radial movement of the lock post 218 relative to the lock post pin 226, while a shape of the cavity 211 within the second arm 207b restricts the lock post 218 to only radial movement. At a radially innermost position available to the lock post 218, the post teeth 217 engage the gear 206, thereby preventing the body 204 and gear 206 from rotating relative to one another about the central axis X in both the clockwise and counterclockwise directions. When the lock post 218 is pushed in to the radially innermost position, such as by pressure on a lock post button 221 on a radially outer end of the lock post 218, the retainer spring 222 biases the retainer 220 into engagement with a post notch 225 of the lock post 218. When engaged in the post notch 225, the retainer 220 prevents the lock post 218 from travelling out of the radially innermost position, so the post teeth 217 remain in engagement with the gear 206 after pressure is removed from the lock post button 221. Pressure may be applied to the retainer 220 through the second arm aperture 223 to compress the retainer spring 221 and move the retainer 220 out of engagement with the post notch 225, thereby releasing the lock post 218 from the radially innermost position. When the retainer 220 is pushed out of engagement with the post notch 225, the lock post spring 224 biases the lock post 218 radially outward and away from the gear 206, freeing the gear 206 and body 204 to rotate relative to one another about the central axis X in the direction permitted by the pawl 208.

Figure 2D:
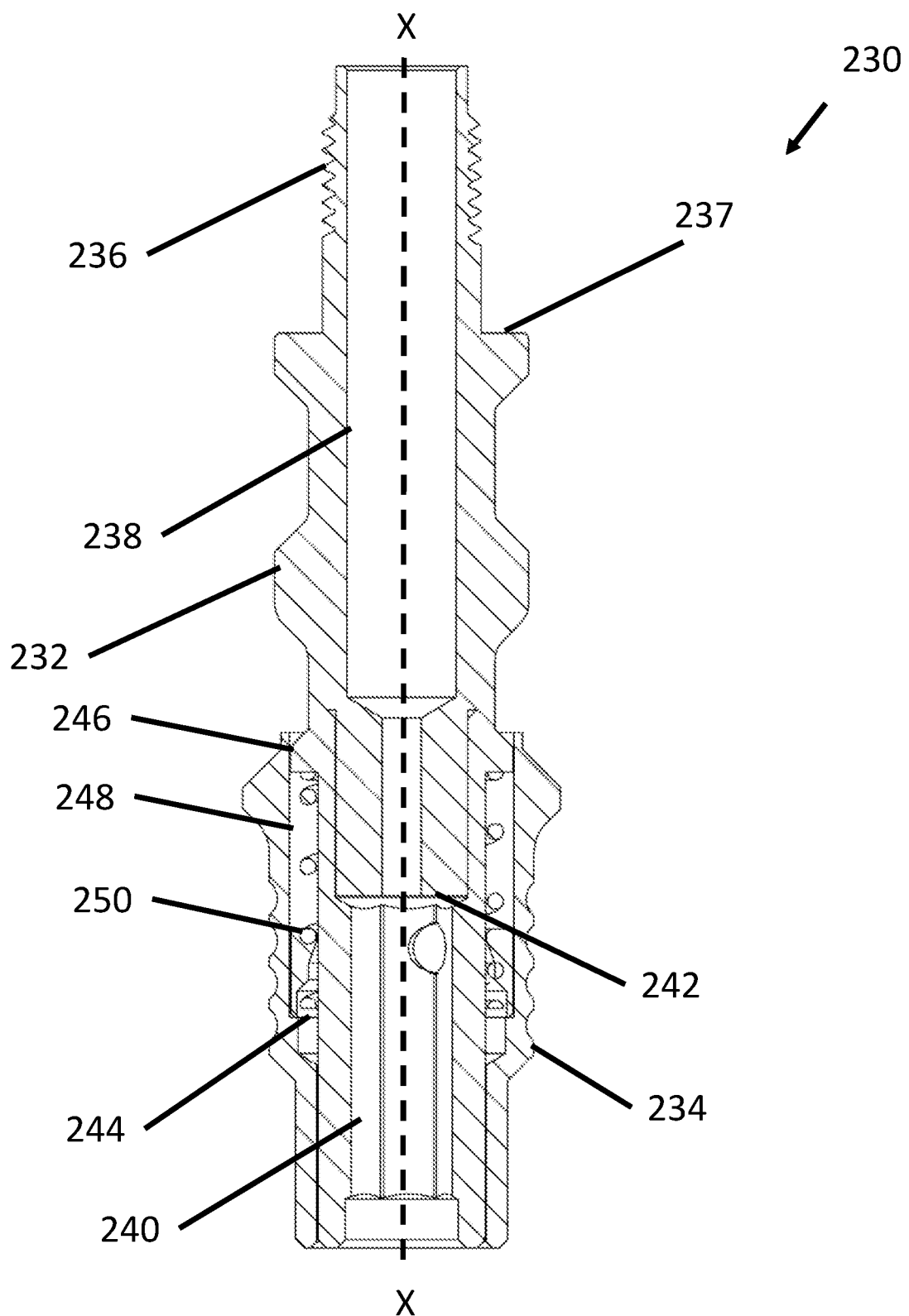
FIG. 2D is a cross-sectional elevation view of an adapter of the handle of FIGS. 2A and 2B.

The distal adapter 230 includes a core 232 and a cover 234 surrounding a distal portion of the core 232 as shown in FIG. 2D. The core 232 in turn includes an axial passage 238 extending through an entire axial length of the distal adapter 230. The axial passage 238 includes a polygonal portion 240 at its distal end. The polygonal portion 240 has a polygonal axial cross-section shaped to receive and drive a polygonal head 418 of the driver 408, shown in FIGS. 4A-4C. As noted above, additional details regarding interaction between a similar handle and drive assembly can be found in the '224 publication. Returning to FIG. 2D, a proximal end of the polygonal portion 240 of the axial passage 238 is defined by an annular shelf 242 extending radially into the axial passage 238. The core 232 is structured to transfer distal axial force on the shoulder 327 to the shelf 242 so that the shelf 242 can, in turn transfer the distal axial force to the polygonal head 418 of the driver 408.

The core 232 and cover 234 include an opposed outer ridge 246 and inner ridge 244, respectively. The outer ridge 246 extends to contact an interior of the cover 234 and the inner ridge 244 extends to contact an exterior of the core 232, so the outer ridge 246 and inner ridge 244 cooperate to define an annular pocket 248 between the core 232 and the cover 234. An adapter spring 250 is disposed within the pocket 248 surrounding the core 232 and extending between the outer ridge 246 and inner ridge 248. The adapter spring 250 thereby acts to bias the cover 234 distally toward a resting position relative to the core 232. Thus, if the cover 234 is forced proximally along the core 232 from the resting position, the adapter spring 250 will bias the cover 234 to return to the resting position when the force is removed.

In arrangements wherein the polygonal head 418 of the driver 408 has an interference fit within the polygonal space 240, a distal portion of the core 232 may expand radially outward around the polygonal space 240 when the polygonal head 418 is inserted. In such arrangements, the cover 234 restricts the expansion of the core 232. The cover 234 may therefore be retracted proximally to facilitate insertion and removal of the polygonal head 418 of the driver 408 into the distal adapter 230.

Figure 2E:
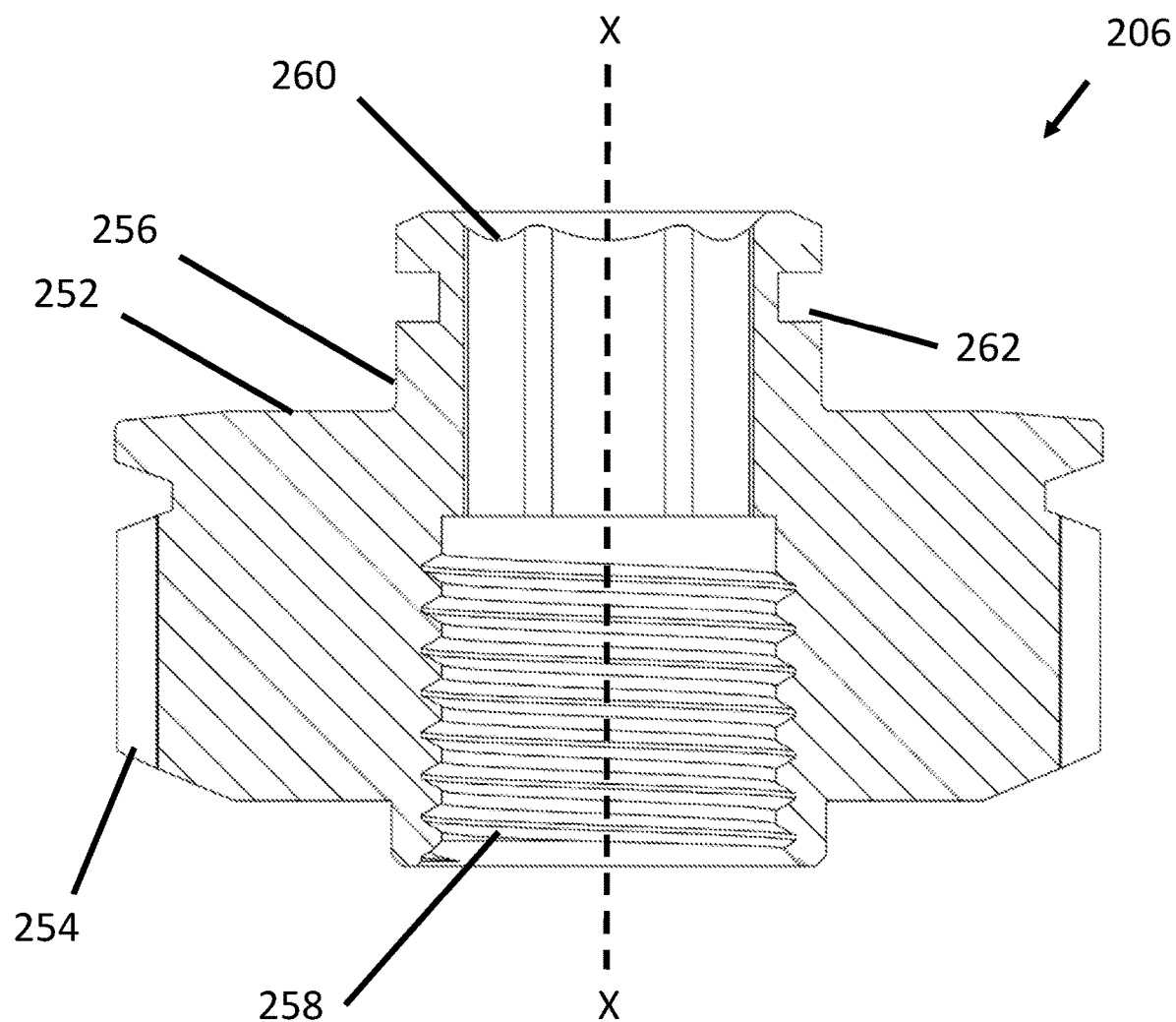
FIG. 2E is a cross-sectional elevation view of the gear of the handle of FIGS. 2A and 2B and the pawl and gear assembly of FIG. 2C.

As shown in FIG. 2E, the gear 206 includes an internal bore 260 extending from its proximal face to its distal face, and a distal portion of the bore 260 includes internal threading 258 for engaging the threaded neck 236 of the distal adapter 230. The gear 206 further includes a teethed portion 252, having the gear teeth 254 for engaging the pawl 208 and post teeth 217, and a raised portion 256. The raised portion 256 has a narrower diameter relative to the central axis X than the teethed portion 252. The raised portion 256 includes an annular groove 262 for engagement with a clip 342 of the stylet holder 300 shown in FIG. 3A.

Figure 3A:
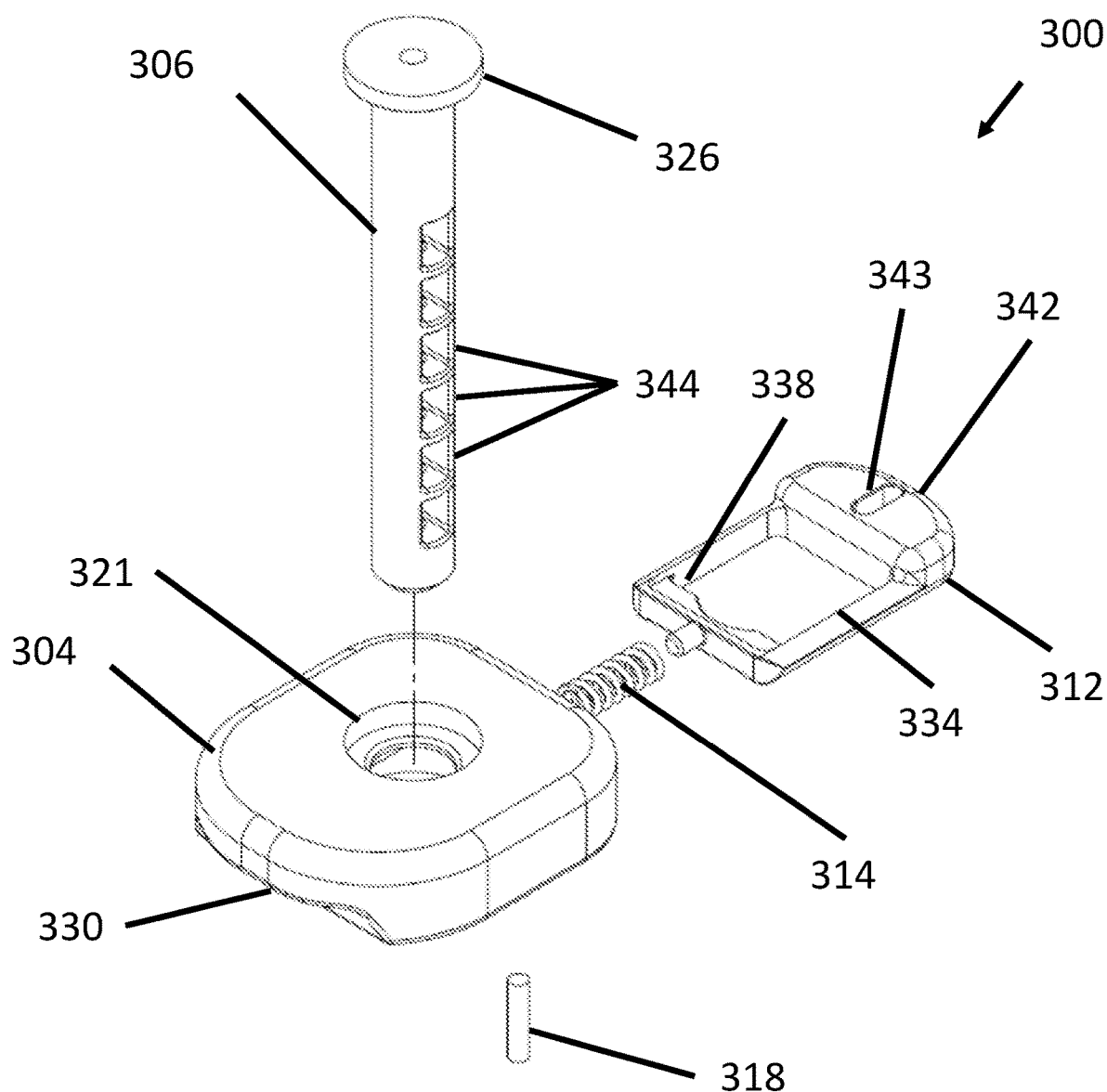
FIG. 3A is an exploded perspective view of a stylet holder of the instrument of FIGS. 1A and 1B.
Figures 3B, 3C:
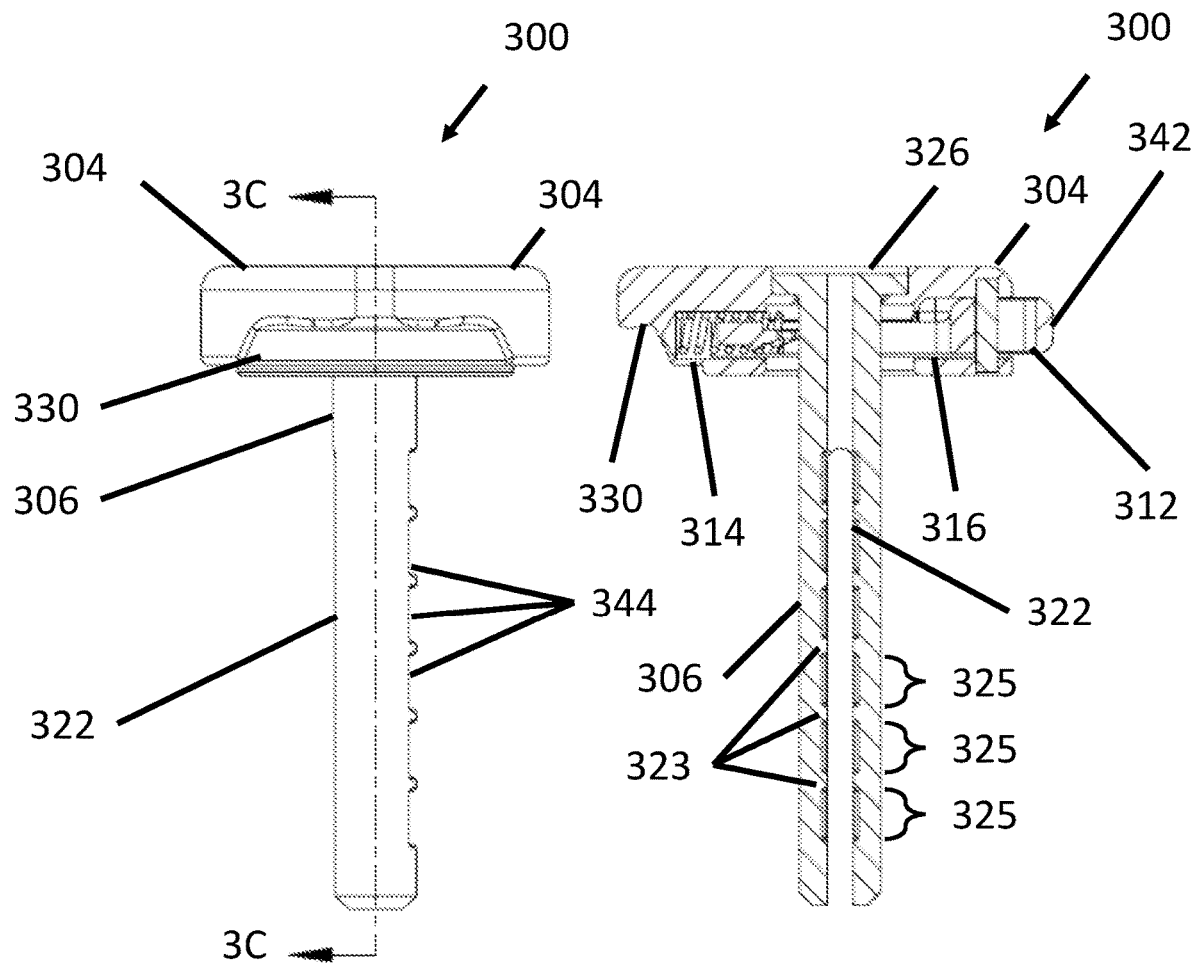
FIG. 3B is a side elevation view of the stylet holder of FIG. 3A.
FIG. 3C is a view along section 3C-3C of FIG. 3B.

The stylet holder 300 illustrated in FIGS. 3A-3C includes a tablet 304, a pillar 306, the clip 312, and a clip spring 314. The clip 312 in turn includes a gap 334, a clip button 342, and a shim 338 that extends into the gap 334. The stylet holder 300 acts as an insert receivable in the handle 200, and retains the stylet 310 in a fixed position when the instrument 100 is assembled as shown in FIGS. 1A or 1B.

In a process for assembling the stylet holder 300 of the illustrated arrangement, the clip spring 214 is into a lateral slot 316 within the tablet 304. Next, the clip 312 is inserted into the lateral slot 316 to push against the clip spring 314. The pillar 306 is inserted from a proximal side of the tablet 304 though a tablet opening 321 and through the gap 334 in the clip 312. The pillar 306 includes a flat head 326 that seats inside a counter bore of the tablet opening 321 such that a proximal face of the tablet 304 and a proximal face of the flat head 326 are coplanar or the flat head 326 is slightly recessed from the proximal face of the tablet 304. The flat head 326 can be secured within the counter bore of the tablet opening 321, such as by adhesive or a weld. The clip pin 318 is inserted through a corresponding hole in the tablet 304 and into the clip track 343. The clip track 343 allows the clip 312 to translate within the lateral slot 314 in a direction perpendicular to the central axis X.

The stylet holder 300 may be installed within the instrument 100 by inserting the pillar 306 into the bore 260 of the gear 206 and the axial passage 238 of the core 230. When the stylet holder 300 reaches an installed location, wherein the tablet 304 is within the proximal face of the tablet 304 is within the handle recess 215 and the proximal face of the tablet 304 is coplanar with or slightly distal of proximal faces of the arms 207a, 207b, the clip 312 may engage the annular groove 262 of the gear 206. The clip spring 314 biases the clip 312 into a position wherein the shim 338 extends into the annular groove 262, thereby coupling the stylet holder 300 to the instrument 100. The clip 312 can be disengaged from the annular gear 206 by applying pressure to the clip button 342 to compress the clip spring 314 and move the shim 338 out of the annular groove 262. The stylet holder 300 and stylet 310 may be removed from the instrument 100 after the clip 312 is disengaged from the annular groove 262, such as by hooking a finger or removal tool under a tablet notch 330 opposite from the clip button 342.

Figure 3D:
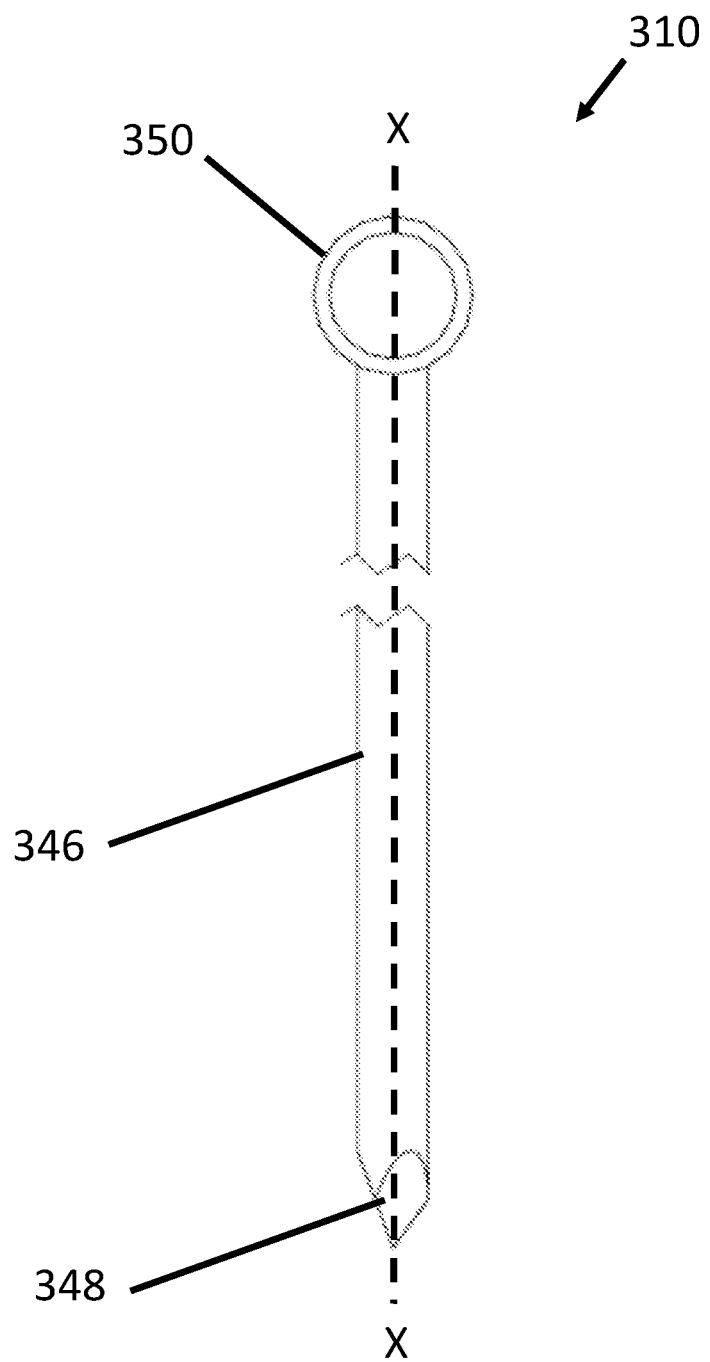
FIG. 3D is a side elevation view of a stylet of the instrument of FIGS. 3A and 3B.

Turning to FIG. 3D, with continued reference to FIGS. 3A-3C, the stylet 310 includes a shank 346 ending distally in a point 348, and ending proximally at a stylet head 350. The stylet head 350 has a cylindrical shape with its circular faces defined on planes parallel to the central axis X. A height of the cylindrical shape of the stylet head 350, defined as a distance between the two circular faces, is greater than a diameter of the shank 346. The pillar 306 of the stylet holder 300 includes an axial channel 322 for accepting the stylet head 350. As shown in FIG. 3C, the channel 322 extends to an external perimeter of the pillar 306 on one side, forming an elongate slot extending axially along the pillar 306 to a distal end of the pillar 306. FIGS. 3A and 3B show a column of pillar apertures 344 extending axially along a side of the pillar 306 opposite from the elongate slot defined by the channel 322. The pillar apertures 344 open into the channel 322. A column of parallel, generally radially extending ribs 323 extends axially down each of two opposed sides of the channel 344, defining an axial column of recesses between the ribs 323 on the two opposed sides of the channel 344. The ribs 323 therefore define opposed pairs of recesses 325 on opposite sides of the channel 322, with each opposed pair of recesses being axially aligned with one of the pillar apertures 344. The opposed pairs of recesses 325 are each shaped and dimensioned to receive the circular faces of the stylet head 350, while a width of the channel 322 between opposed pairs of ribs 323 is less than the height of the cylindrical shape of the stylet head 350, but greater than or equal to the diameter of the shank 346. The opposed pairs of recesses 325 and pillar apertures 344 thus define discrete, predefined locations along the central axis X wherein the stylet holder 300 can retain the stylet head 350.

To prepare the instrument 100 for use, the stylet head 350 is slotted into the channel 322 of the pillar 306 such that the two circular faces of the stylet head 350 are received in an opposed pair of recesses 325 and edge of the stylet head 350 extends into the pillar aperture 344 axially aligned with the opposed pair of recesses. A fit of the stylet head 350 within the opposed pair of recesses 325 and the pillar aperture 344 allows the stylet head 350 to rotate relative to the pillar 306. The stylet 310 is then turned to axially align the shank 346 with the pillar 306 within the channel 322. The stylet 310 is then be inserted through the bore 260 of the gear 206 and guided through the instrument 100 to protrude from a distal end of the driver 408. The stylet holder 300 is inserted into the instrument 100 and coupled to the handle 200 via the annular groove 262 of the gear 206 as discussed above.

With the stylet holder 300 installed within the instrument 100 while the stylet head 350 is disposed within the channel 322, the stylet 310 is largely constrained into alignment with the central axis X of the instrument 100. The pillar 306 extends into the axial passage 238 of the distal adapter 230, and the axial passage 238 of the distal adapter 230 is dimensioned to prevent the stylet head 350 from exiting the channel 322. Other features that the shank 346 passes through between the axial passage 238 of the distal adapter 230 and the distal end of the driver 408 are narrower than the axial passage 238, and therefore serve to further constrain the stylet 310 within the instrument 100.

Figure 4A:
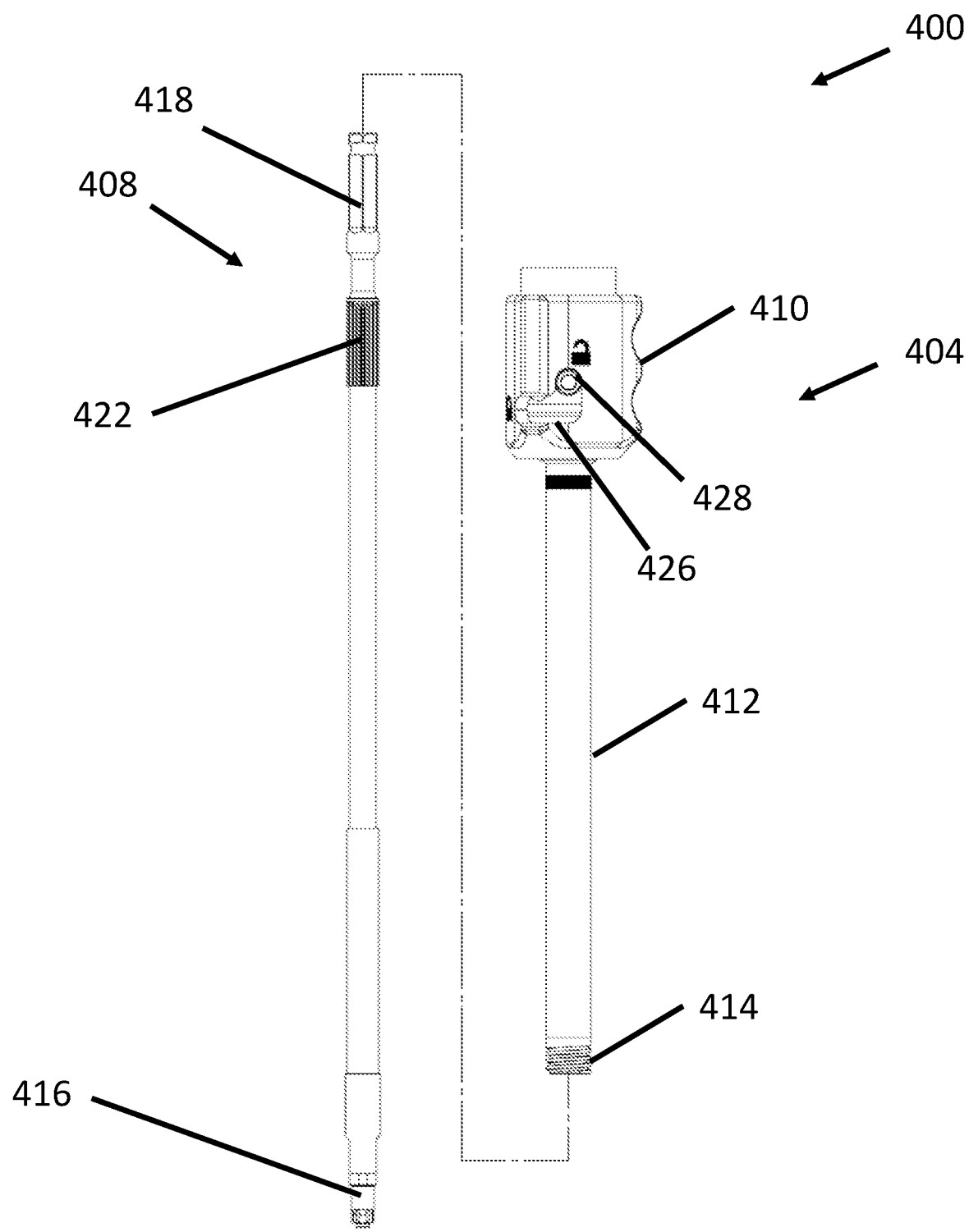
FIG. 4A is a side elevation view of a drive assembly of the instrument of FIGS. 1A and 1B in a disassembled state.
Figures 4B, 4C:
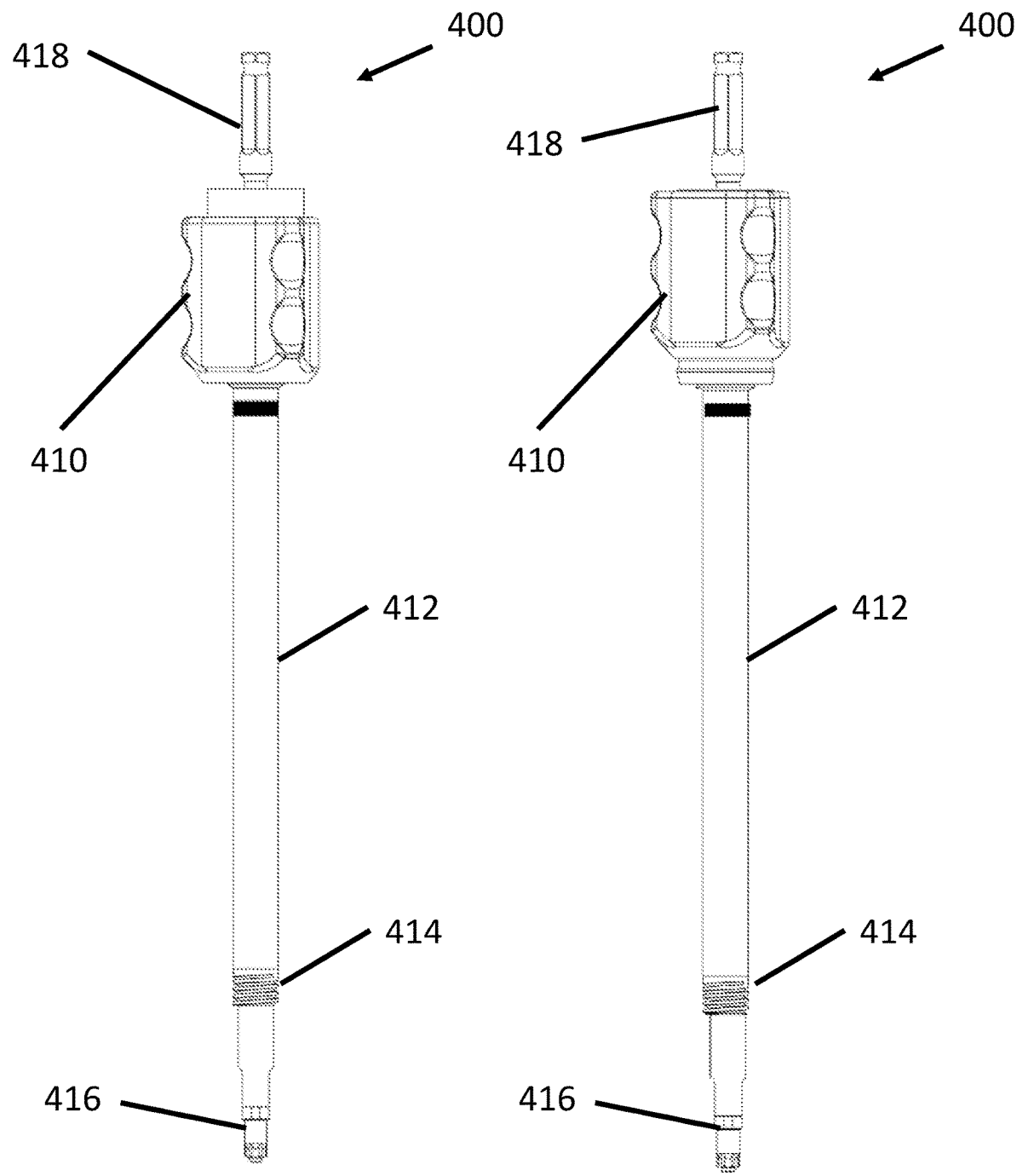
FIG. 4B is a side elevation view of the drive assembly of FIG. 4A in an unlocked position.
FIG. 4C is a side elevation view of the drive assembly of FIGS. 4A and 4B in a locked position.

Selection and placement of the stylet 310 may be in view of details specific to a patient, operation, or fastener. For example, in some arrangements, the stylet 310 is selected or constructed to have a desired length determined in view of the instrument 100 and the screw 110. In further arrangements, the opposed pair of recesses 325 and pillar aperture 344 into which the stylet head 350 is disposed before the stylet holder 300 is inserted into the handle 200 are selected in view of the length of the stylet 310, instrument 100, and screw 110. In further arrangements, the length of the stylet 310, the opposed pair of recesses 325 and aperture 344, or both, are selected such that the point 348 of the stylet 310 will be a predetermined distance from a tip of the screw 110 when the instrument 100 is fully assembled. In yet further arrangements, the predetermined distance is 5 mm, 10 mm, or 15 mm The drive assembly 400 includes the sheath assembly 404 and the driver 408, which is insertable through the sheath assembly 404 as shown in FIGS. 4A-4C such that the distal end of the driver 408, defined by a drive head 416, extends distally beyond the tube 412. The drive head 416 is any known screw driving feature suitable for driving engagement with a head of the screw 110. For a more detailed description of an exemplary drive head and engagement thereof with an exemplary bone screw, reference can be made to the '724 patent. The knob 410 is axially actuatable relative to the tube 412 of the sheath assembly 404 between a locked position, wherein the sheath assembly 404 is rotationally coupled to the driver 408, and an unlocked position, wherein the sheath assembly 404 is free to rotate relative to the driver 408. In the illustrated example, the unlocked position, shown in FIG. 4B, is distal of the locked position, shown in FIG. 4C.

Assembly of the instrument 100 of the illustrated arrangement includes inserting the driver 408 into the sheath assembly 404. The sheath assembly 404, with the knob 410 in the unlocked position, is rotated about the driver 408 to thread the threaded portion 414 of the tube 412 into engagement with the extension assembly 120. For a more detailed description of the interaction between an exemplary driver and extension assembly as may be modified for use with the instrument 100 of the present disclosure, reference can again be made to the '724 patent. The knob 410 is then actuated to the locked position to rotationally couple the sheath assembly 404 to the driver 400. In the illustrated example, the knob 410 includes an L-shaped track 426 in cooperation with a boss 428 extending radially outward from the tube 414 and through the L-shaped track 426, permitting the knob 410 to rotate about the tube 414 a short distance when the knob 410 is in the locked position. The user may therefore turn the knob 410 after actuating the knob 410 to the locked position to locate the boss 428 away from a vertical leg of the L-shaped track, enabling the application of axial force on the knob 410 without moving the knob 410 to the unlocked position. Rotational force on the knob 410 is transferred to the tube 412 by edges of the L-shaped track 426 bearing on the boss 428.

In some arrangements, the rotational coupling and uncoupling of the sheath assembly 404 and driver 408 is achieved by cooperation of internal contours and a moveable spline element (not illustrated) within the knob 410. The spline element is axially and rotationally coupled to the tube 412, but axially uncoupled from the knob 410. Axial actuation of the knob 410 therefore causes the internal contours of the knob to move relative to the spline element while the spline element remains in a constant axial location relative to the tube 412. Movement of the knob 410 axially into the locked position causes the internal contours of the knob 410 to guide the spline element radially into engagement with the splined portion 422 of the driver 408, thereby rotationally coupling the tube 412 and sheath assembly 404 to the driver 408. Similarly, movement of the knob 410 axially into the unlocked position causes the internal contours of the knob 410 to guide the spline element radially out of engagement with the spline portion of the driver 408, thereby rotationally uncoupling the tube 412 and sheath assembly 404 from the driver.

For a more detailed description of locking and unlocking of a similar knob and drive assembly, reference can be made to the '553 patent.

The instrument 100 and its components described above may be made of any material or combination of materials suitable for driving known screws into solid objects. In medical applications particularly, biocompatible or non-toxic materials are preferred, as are materials that are suitable for sterilization and repeated use. Stainless steel, titanium, and alloys thereof are specifically contemplated as suitable for any part of the driver. However, some components, including but not limited to the handle body 204, adapters 202, 230, block 210, post 221, washer 228, or any sub-components thereof, may be made of any of a wide variety of rigid polymers. Additionally, any component of the instrument other than necessarily flexible components such as springs or the core 232 of the distal adapter 230 may be made of ceramic.

Figure 5:
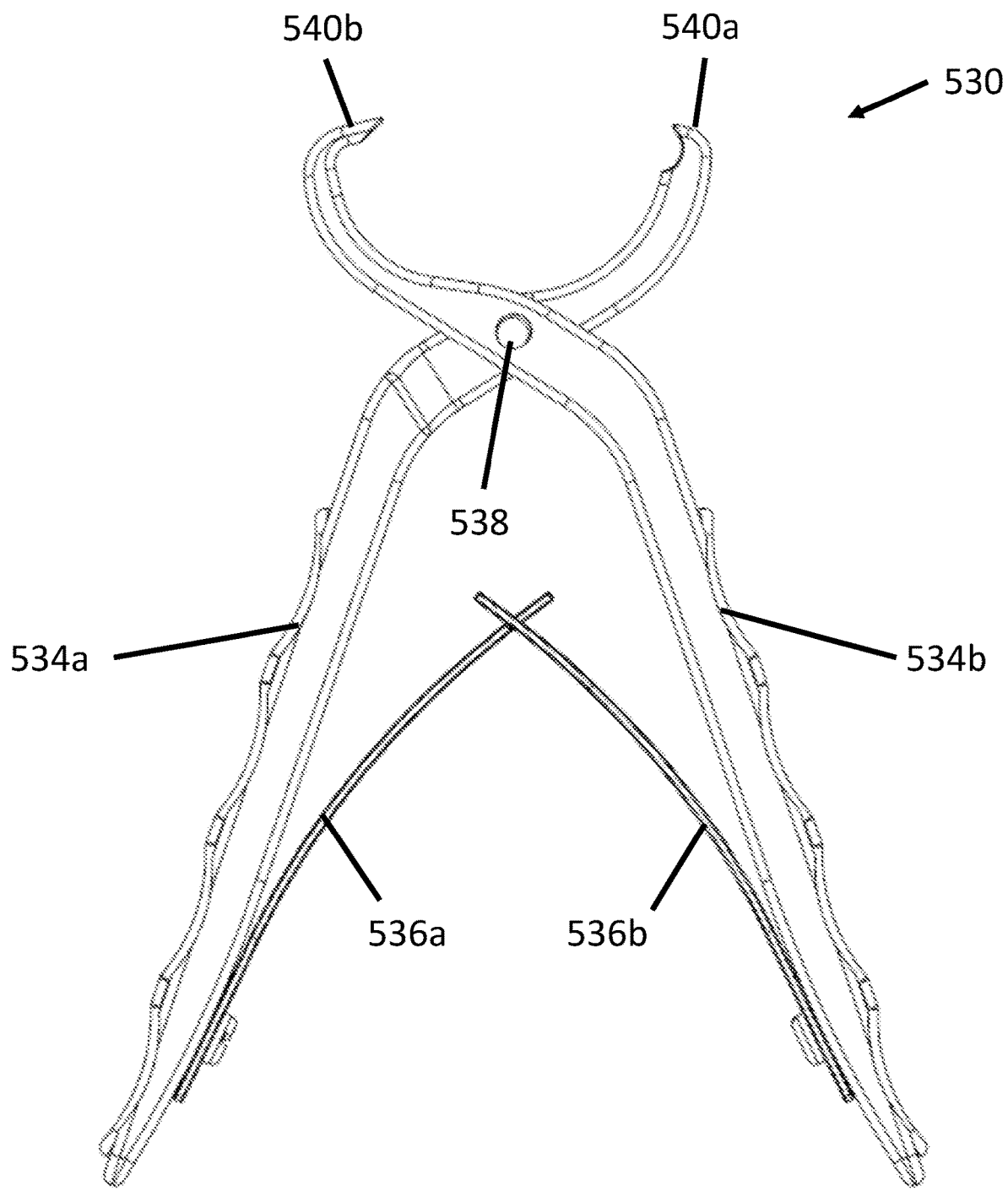
FIG. 5 is a side elevation view of a removal tool for use with the instrument of FIGS. 1A and 1B.

FIG. 5 illustrates a removal tool 500 for removing the stylet holder 300 and stylet 310 from the instrument 100. The removal tool 500 includes a first grip 534a and a second grip 534b joined at a hinge 538. A first leaf spring 536a and second leaf spring 536b are attached to the first grip 534a and second grip 534b, respectively, and at rest curve toward the opposite grip 534a, 534b. The grips 534a, 535b of the illustrated arrangement are wider than the leaf springs 536a, 536b, so the leaf springs 536a, 536b may pass by each other to contact the opposite grip 534a, 534b.

The first grip 534a is integrally connected to a hook 540a on an opposite side of the hinge 538, and the second grip 534b is integrally connected to a wedge 540b on the opposite side of the hinge 538. The hook 540a is shaped to match a contour of the clip button 342, and the wedge 540b is shaped to slide under the tablet notch 330. The removal tool 500 therefore cooperates with shapes of the tablet 304 and clip 312 to facilitate removal of the stylet holder 300 and styled 310 from the instrument. The removal tool 500 may be positioned such that when the grips 534a, 534b are drawn close to one another, the hook 540a covers the clip button 342, and the wedge 540b slides under the tablet notch 330. The hook 540a pushes the clip button 342 to disengage the clip 312 from the annular groove 262 of the gear 206 while the wedge 540b pushes the tablet 304 proximally. The removal tool 500 can therefore be used to easily remove the stylet holder 300 and stylet 310 from the instrument 100.

As noted above with regard to the instrument 100, the removal tool 500 can be made from any of a variety of materials including metals, such as stainless steel, titanium, or alloys thereof, rigid polymers, or, with the exception of the leaf springs 536a, 536b, ceramic. Again, in medical applications, materials that are non-toxic, biocompatible, and conducive to sanitization and reuse are preferred.

In an exemplary process for use of the instrument 100, the handle 200, stylet holder 300, and drive assembly 400 are separately assembled, as described above. The extension assembly 120 is coupled to the screw 110. A stylet 310 is constructed at a desired length or selected from a plurality of stylets 310 having various predetermined lengths. The drive assembly 400 is inserted into the extension assembly 120. The drive head 416 is positioned for driving engagement with the head of the screw 110. With the knob 410 in the unlocked position, the drive assembly 400 is rotated about the driver 408 such that the threaded portion 414 of the tube 410 engages the extension assembly 120, thereby retaining the drive head 416 in driving engagement with the head of the screw 110. The knob 410 is then actuated to the locked position. The cover 234 of the distal adapter 230 of the handle 200 is retracted proximally relative to the core 232 while the polygonal head 418 of the driver 408 is inserted into the polygonal portion 240 of the axial passage 238 of the distal adapter 230. After the polygonal head 418 is seated against the annular shelf 242 of the distal adapter 230, the cover 234 is allowed to return distally over the core 232, compressing the core 232 around the polygonal head 418. The stylet 310 is disposed within one of multiple discrete, predefined locations within the stylet holder 300, each of the predefined locations corresponding to the pillar apertures 344 and opposed pairs of recesses 325 in the pillar 306 such that the stylet 310 will extend a desired distance distally beyond the tip of the screw 110 when the instrument 100 is fully assembled. The stylet 310 and stylet holder 300 are inserted into the handle 200 such that the stylet 310 extends through the handle 200, drive assembly 400, and screw 110, and the clip 312 engages the annular groove 262 on the raised portion 256 of the gear 206. The foregoing steps may be performed in any order that results in an assembled instrument 100 generally as shown in FIGS. 1A and 1B.

The point 348 of the stylet 310 is used to pierce an exterior surface of a solid object, such as a bone, or specifically a vertebral pedicle, thereby providing a pilot hole. Force is applied to the instrument 100 until the tip of the screw 110 enters the pilot hole. The handle 200 is used to drive the screw 110 into the object. Action of the pawl 208 on the gear 206 provides the handle 200 with a ratcheting function, such that torque applied to the handle 200 in a direction that drives the screw 110 into the object is transferred to the screw 110, but torque applied to the handle 200 in an opposite direction causes the handle 200 to rotate relative to the instrument 100 without being transferred to the screw 110. When the screw 110 reaches a desired depth in the object, the extension assembly is decoupled from the screw 110 and the instrument 100 is withdrawn. At any stage after the screw 110 engages the pilot hole, the stylet holder 300 and stylet 310 are removed from the instrument 100 by pulling proximally on the tablet 304 by hand or with the removal tool 500. If necessary at any stage, torque is applied to the instrument 100 beyond the handle 200 in a direction opposite from that used to drive the screw 110 into the object by depressing the post button 221 to cause the post teeth 217 to lock the gear 206 relative to the body 204 of the handle 200 before turning the handle 200. Ratcheting function is then restored by depressing the retainer 220 to allow the post 218 to return radially outward and disengage the gear 206.

For additional details regarding a method of driving a screw into a vertebral pedicle using a stylet as a guide, reference can be made to the '224 publication.

Although the concepts herein have been described with reference to particular embodiments, it is to be understood that these embodiments are merely illustrative of the principles and applications of the present disclosure. It is therefore to be understood that numerous modifications may be made to the illustrative embodiments and that other arrangements may be devised without departing from the spirit and scope of the present disclosure as defined by the appended claims.

The invention claimed is:

1. A screw driving instrument, comprising:
   a handle;
   a passage extending through the handle and along a central axis of the instrument; and
   an insert receivable in a portion of the passage extending through the handle, the insert including:
   a clip engageable to the handle;
   a stylet including a stylet head; and
   a pillar including a channel defining an elongate slot, a plurality of recesses, and a plurality of apertures axially aligned with the plurality of recesses, wherein the recesses define a plurality of discrete positions wherein the stylet head may be received in the channel,
   wherein the recesses are defined by a column of convex ribs radially extending along each opposed side of the channel, and
   wherein the plurality of apertures are defined on two opposed sides of the pillar, each aperture of the plurality of apertures being open on one side of the pillar and closed on an opposite side of the pillar.

2. The screw driving instrument of claim 1, wherein the plurality of apertures comprises a column of apertures opening into the channel and extending along an opposite side of the pillar from the elongate slot, each aperture being axially aligned with one of the recesses.

3. The screw driving instrument of claim 1, wherein the plurality of recesses comprises opposed pairs of recesses defined on two opposed sides of the channel.

4. The screw driving instrument of claim 3, wherein the plurality of apertures comprises a column of apertures opening into the channel and extending along an opposite side of the pillar from the elongate slot, each aperture being axially aligned with one of the opposed pairs of recesses.

5. The screw driving instrument of claim 1, wherein the handle includes a ratchet mechanism comprising:

a gear disposed within a body of the handle and including an axial bore through which the insert is insertable; and a pawl fixed to the handle allowing rotation of the body of the handle relative to the gear in only one direction about the central axis of the instrument.

6. The screw driving instrument of claim 5, wherein the ratchet mechanism comprises a post disposed within the body of the handle and having a radially inner end with post teeth, the post being actuatable between a radially inner position wherein the post teeth engage the gear and prevent rotation of the body of the handle relative to the gear about the central axis of the instrument and a radially outer position wherein the post teeth do not engage the gear.

7. A screw driving instrument, comprising:
a cannulated drive shaft including a distal end defining a drive head and extending along a central axis of the instrument;
a stylet including a proximal end defining a stylet head;
a stylet holder engageable to the instrument and including a pillar including a channel defining a plurality of recesses and a plurality of apertures axially aligned with the plurality of recesses, the pillar configured to retain the stylet head in the channel at one of a variety of discrete positions relative to the instrument while the stylet holder is coupled to the instrument,
wherein the recesses are defined by a column of convex ribs radially extending along each opposed side of the channel, and
wherein the plurality of apertures are defined on two opposed sides of the pillar, each aperture of the plurality of apertures being open on one side of the pillar and closed on an opposite side of the pillar.

8. The screw driving instrument of claim 7, wherein the stylet holder is couplable to the instrument such that the stylet head is not removable from the pillar while the stylet holder is coupled to the instrument.

9. The screw driving instrument of claim 7, comprising a ratcheting handle.

10. The screw driving instrument of claim 9, wherein the ratcheting handle is releasably engageable with the drive shaft.

11. The screw driving instrument of claim 9, wherein the handle includes a gear and pawl assembly providing ratcheting function to the handle, the gear including a bore through which the pillar is received while the stylet holder is coupled to the instrument.

12. The screw driving instrument of claim 9, wherein reversible coupling between the stylet holder and the instrument is facilitated by a clip of the stylet holder being engageable with the gear.

13. The screw driving instrument of claim 9, wherein the handle is reversibly lockable such that ratcheting is prevented while the handle is locked.

14. A method of use of a screw driving instrument, the method comprising:
disposing a portion of a stylet within a stylet holder, the pillar including a channel defining a plurality of recesses and a plurality of apertures axially aligned with the plurality of recesses, the pillar capable of retaining the portion of the stylet at multiple locations along an axis of the channel such that the portion of the stylet is retained at one of the multiple locations along the axis; and
inserting the stylet and stylet holder into the instrument such that a distal end of the stylet extends out of a distal end of the instrument while the portion of the stylet is retained at the one of the multiple locations along the axis,
wherein the recesses are defined by a column of convex ribs radially extending along each opposed side of the channel, and
wherein the plurality of apertures are defined on two opposed sides of the pillar, each aperture of the plurality of apertures being open on one side of the pillar and closed on an opposite sid eof the pillar.

15. The method of claim 14, comprising:
creating a pilot hole in a solid object with the stylet;
introducing a screw into the pilot hole with the instrument; and
removing the stylet holder and stylet from the instrument after introducing the screw into the pilot hole.

16. The method of claim 15, wherein the stylet holder is removed from the instrument by use of opposed ends of a removal tool to simultaneously depress a button to decouple the stylet holder from the instrument with one of the opposed ends and wedge between the instrument and stylet holder with another of the opposed ends.

17. The method of claim 14, wherein the multiple locations along the axis are discrete and predefined.

18. The method of claim 17, wherein the multiple locations along the axis are predefined by recesses extending axially along at least one side of a channel extending along a portion of the stylet holder.

19. The method of claim 14, wherein the instrument includes a ratcheting handle capable of being locked to reversibly disable ratcheting.

* * * * *